United States Patent [19]
Pastyr et al.

[11] Patent Number: 4,794,629
[45] Date of Patent: Dec. 27, 1988

[54] CONTOUR COLLIMATOR FOR RADIATION THERAPY

[75] Inventors: Otto Pastyr, Leimen; Wolfgang Maier-Borst, Dossenheim, both of Fed. Rep. of Germany

[73] Assignee: Siemens Aktiengesellschaft, Berlin and Munich, Fed. Rep. of Germany

[21] Appl. No.: 50,323

[22] Filed: May 14, 1987

[30] Foreign Application Priority Data

May 14, 1986 [DE]   Fed. Rep. of Germany ....... 3616141
Apr. 3, 1987 [DE]   Fed. Rep. of Germany ....... 3711245

[51] Int. Cl.⁴ .............................................. G21K 1/04
[52] U.S. Cl. .................... 378/152; 378/150; 378/146; 378/65
[58] Field of Search ................ 378/64, 65, 145–147, 378/150–152; 250/363 SH

[56] References Cited

U.S. PATENT DOCUMENTS

| | | | |
|---|---|---|---|
| 4,463,266 | 7/1984 | Brahme | 378/150 |
| 4,672,652 | 6/1987 | Hüttenranch et al. | 378/150 |
| 4,739,173 | 4/1988 | Blosser et al. | 378/152 |

FOREIGN PATENT DOCUMENTS 192300  12/1906  Fed. Rep. of Germany .
1010659  6/1957  Fed. Rep. of Germany .
3030332  2/1982  Fed. Rep. of Germany .

OTHER PUBLICATIONS

"Confirmation Radio Therapy", Takahashi, Acta Radiologica, Suppl., 242, (1965).

Primary Examiner—Craig E. Church
Assistant Examiner—John C. Freeman
Attorney, Agent, or Firm—Hill, Van Santen, Steadman & Simpson

[57] ABSTRACT

A contour collimator has diaphragm plates arranged in displaceable fashion relative to one another. Each diaphragm plate is individually engageable with an adjustment element shared by all of the diaphragm plates for displacing one diaphragm plate relative to the remaining diaphragm plates. An interlock mechanism in engagement with the remaining diaphragm plates retains those plates in their respectively existing positions during displacement of the one plate. The adjustment element is displaceable from the one diaphragm plate to another diaphragm plate which can then be displaced by the adjustment element while the other plates are retained in position.

40 Claims, 6 Drawing Sheets

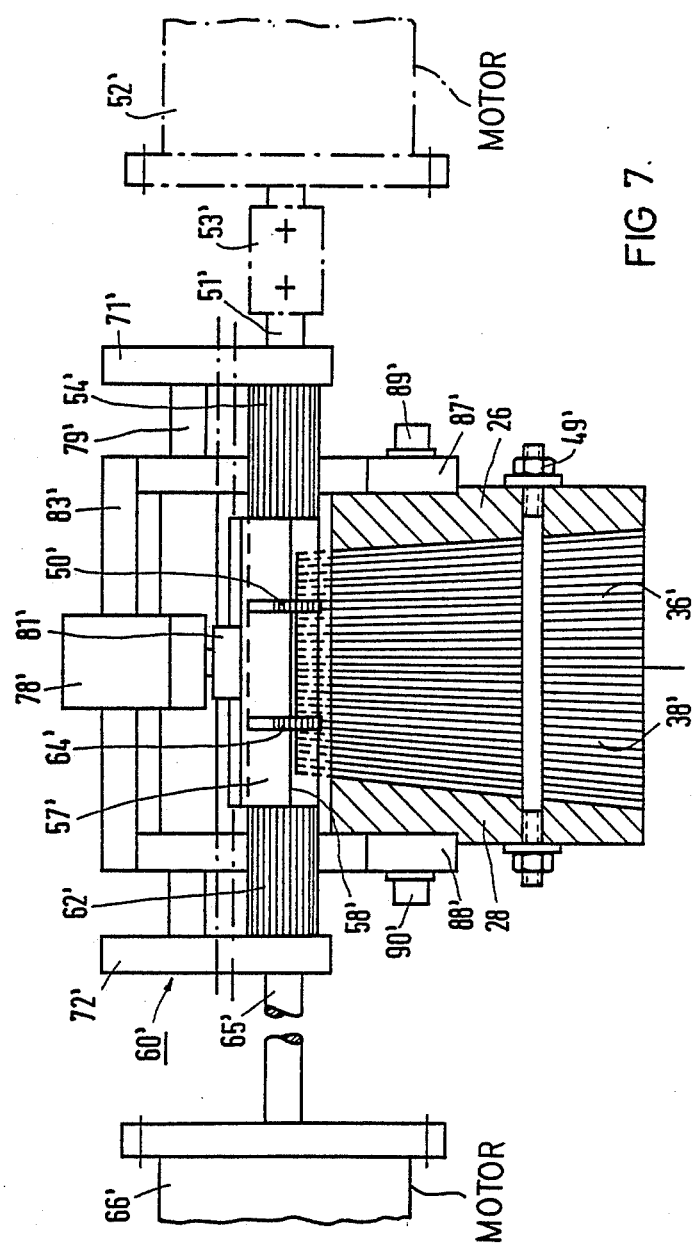

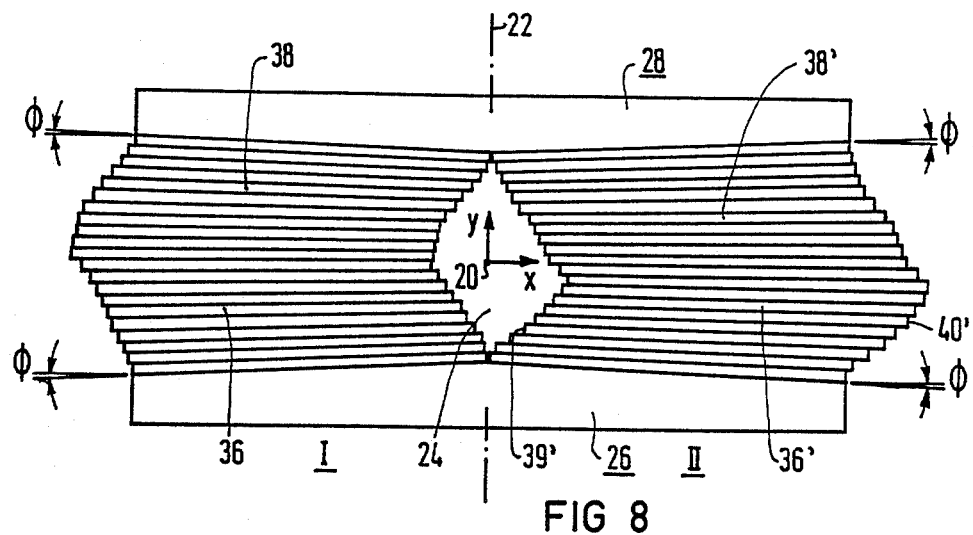
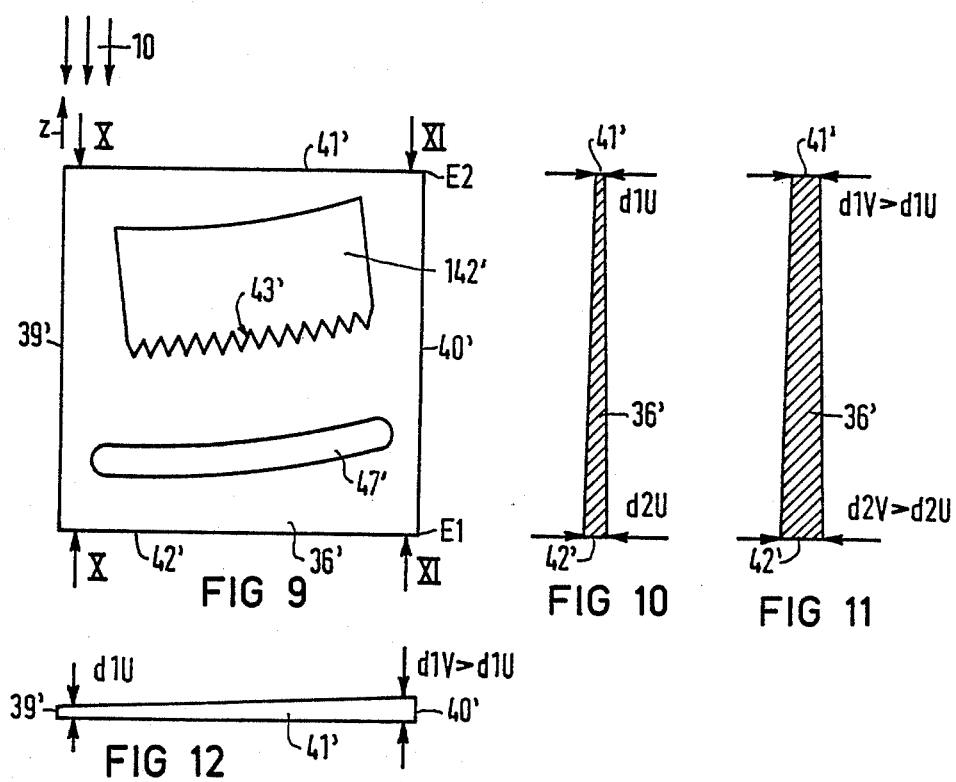

CONTOUR COLLIMATOR FOR RADIATION THERAPY

BACKGROUND OF THE INVENTION

1. Field of the Invention

The invention is directed to a contour collimator for radiation therapy having a prescribed plurality of diaphragm plates displaceably arranged relative to one another. It is particularly directed to a multi-leaf collimator that is utilized for limiting the radiation field of an ionizing radiation, preferably for limiting the radiation field of gamma radiation in a linear accelerator.

2. Description of the Prior Art

Radiation apparatus employed in oncological radiation therapy are equipped with radiation field collimators which only allow the adjustment of rectangularly limited radiation fields. It is currently known, however, that better therapy results could be achieved in many oncological investigations if the radiation dose distribution could be adapted to the usually irregular shape of the target volumes (tumors are usually not spherical).

To this end, irregularly shaped auxiliary collimators are individually fabricated for use in radiation therapy. The equipment required for the manufacture of such collimators is commercially available. Such equipment enables irregular radiation field shapes to be cut out of rigid plates of expanded plastic on the basis of X-ray picture models and to cast the part with metal alloys having a low melting point. This manufacturing procedure can only be carried out given individual irradiation angles and is rather involved.

The use of arbitrarily adjustable collimators based on the multi-leaf principle (what are referred to as "multi-leaf collimators") was proposed by Takahashi as early as 1965 ("Confirmation Radio Therapy", Acta Radiologica, Suppl. 242 (1965), 1–142). Such manually adjustable collimators were then likewise utilized worldwide in various radio therapy centers in the further course of radiation therapy. The advantage over collimators manufactured in accord with the casting principle, however, is slight. Cutting out and casting is replaced by the likewise time-consuming manual adjustment of the individual "collimator leafs" or "diaphragm plates".

The development of motor-adjustable multi-leaf collimators is currently being pursued at many radio therapy centers in view of the availability of inexpensive microelectronic control components. These collimators are provided for employment at neutron irradiation systems, at photon radiation sources and, in particular, at linear accelerators. These unit share the principle of the single-leaf drive. Every leaf (diaphragm plate) of the multi-leaf collimator is driven by its own stepping motor. The number of required stepping motors is identical to the number of individual leaves. The outlay for complicated electronics which is susceptible to malfunction and the space requirement for the integration of such a collimator into an iradiation installation is extremely high since a total of at least forty leaves and, as a result thereof, forty stepping motors, is required.

German patent No. 192 300 discloses a contour collimator wherein two oppositely arranged groups of mutually displaceable, small rods impermeable to X-rays are provided for admitting only a prescribed profile from the radiation field of an X-ray source. This collimator is not suitable for radiation therapy wherein, in particular, high-energy photons (gamma radiation) are employed, since no actual "diaphragm plates" are employed. Moreover, only a manual adjustment of the small rods is provided. Such a manual adjustment, however, is usually too slow for radiation therapy, wherein a plurality of radiation fields having different profiles are successively applied.

German AS No. 1 010 659 discloses a collimator for shaping a useful radiation beam from the radiation of a high-energy radiator, for example a cobalt-60-preparation, comprising diaphragm plates which are adjustable to be shaped. In this collimator, a separate adjustment perpendicularly relative to the central ray of the beam to be shaped. In this collimator, a separate adjustment element is provided for every individual diaphragm plate. A drive element, for example, a drive shaft shared by all adjustment elements is connected to each of the adjustment elements only via friction clutches. The limitation of the desired radiation field is prescribed by a perforated plate into which pins are plugged. Given such a collimator, it is difficult to set a new radiation field within a short time. Moreover, the collimator is not suitable for oscillations in a vertical plane. In a certain position, the sliding clutch responds under the influence of the weight of the collimator plates; diaphragm plates would thus fall out, and a change in the contour results. Further, a sliding clutch does not guarantee the patient safety in what is referred to as a one-time irradiation in which the total dose required is applied in fractions as the radiation source and collimator are moved around the patient.

German patent No. 30 30 332 discloses a primary radiation diaphragm for an X-ray examination installation wherein a plurality of gating elements limiting the radiation cone from various sides are employed, these being composed of thin metal strips pressing against one another. The elements are mutually displaceable in the longitudinal direction and are combined in packets. For remotely controllable adjustment, every metal strip carries a nose extending transversely relative to the displacement direction and perpendicularly relative to the gating plane. The nose is disposed at the side of the element facing away from the symmetry axis of the primary radiation diaphragm. Every metal strip packet has an adjustment element allocated to it, this adjustment element being adjustable by an x, y-drive and being engageable with the individual metal strips. This contour collimator is only suitable for low energies since relatively short diaphragm plates are employed. Given a 360° rotation of the collimator around a patient, the individual diaphragm plates would fall out because no interlock is provided. An adjustment element for the individual diaphragm plate is provided, but this can only move low diaphragm plate weights. As a result of its design, moreover, this is limited only to the adjustment of softly shaped contours or profiles, i.e. contours or profiles without steps.

SUMMARY OF THE INVENTION

An object of the present invention is to fashion a contour collimator of the type initially cited such that a simple, finely stepped adjustability of the diaphragm plates is guaranteed with low outlay, whereby an adequate security against the maladjustment of a selected radiation contour is simultaneously established.

This object is achieved in accordance with the principles of the present invention in a collimator having:
(a) teeth at every diaphragm plate, (b) an adjustment element shared by the prescribed plurality of diaphragm plates for the adjustment of a first diaphragm plate relative to the remaining diaphragm plates, this adjustment element being in engagement with the teeth of the first diaphragm plate, (c) an interlock mechanism in engagement with the teeth of the remaining diaphragm plates, and (d) a mechanism for displacing the adjustment element from the teeth of the first diaphragm plate to the teeth of a neighboring, second diaphragm plate, the first diaphragm plate being locked during this displacement and the second diaphragm plate being unlocked.

The second diaphragm plate need not be the plate placed immediately next to the first diaphragm plate; it can also be a further diaphragm plate.

What is guaranteed in such a contour collimator is that the contour set for a prescribed irradiation direction does not automatically change. As a result thereof, the collimator is especially suited for application in combination with radiation sources which move during the irradiation. In particular, this collimator can be utilized when circling around a tumor to be irradiated. Tumors are normally irregularly shaped. In radiation therapy, they are usually approached from various irradiation directions. The through aperture or contour of the contour collimator in continuous or stepped revolution around the tumor can thus be quickly adapted to its respectively current contour, i.e. the contour seen from the irradiation direction. This enables short irradiation times, being particularly significant for high-energy gamma radiation which is generated by a linear accelerator. Given a known profile of the tumor which, for example, can be identified by a computer tomograph exposure and by three-dimensional calculation and irradiation planning following thereupon, the contour can be motor-adjusted when circling around without having to fear that individual diaphragm plates will change their established position or will even fall out. What is thereby achieved is that the tumor is irradiated tightly bounded and healthy tissue is optimally preserved.

In one embodiment of the invention a further prescribed plurality of diaphragm plates is arranged next to the first-cited diaphragm plate, and an identically constructed interlock and displacement mechanism is allocated to these further diaphagm plates. In this way, a displacement of diaphragm plates for the purpose of adjustment of a new contour can be carried out from two sides, which shortens the access time and thus the irradiation duration.

A further embodiment has a symmetrical structure with respect to a center line. Packets of diaphragm plates which are respectively displaceable relative to one another are thus arranged at both sides of this center line. The diaphragm plates of the two packets are thereby arranged so as to be moveable toward one another. The arrangement is preferably undertaken such that the diaphragm plates can be respectively swiveled beyond the center line into the region of the other packet of diaphragm plates. Asymmetrical radiation fields can be set in this way.

Given a suitable selection of the tooth spacings in the teeth of every diaphragm plate, the individual diaphragm plates can be displaced to a greater or lesser degree in the direction toward the center line in fine steps. The desired irradiation profile can be set with great precision in this way.

DESCRIPTION OF THE DRAWINGS

FIG. 7 is a sectional view taken along line C—C through the right part of the contour collimator of FIG. 2.

FIG. 8 is a view from above of a portion of another embodiment of contour collimator in accord with the invention.

FIG. 9 is a side view of a diaphragm plate that is utilized in the right front diaphragm plate packet group of FIG. 8.

FIG. 10 is a section through the left part of the diaphragm plate of FIG. 9 along the line X—X.

FIG. 11 is a section through the right part of the diaphragm plate of FIG. 9 along the line XI-XL.

FIG. 12 is a plan view of the diaphragm plate of FIG. 9.

DESCRIPTION OF THE PREFERRED EMBODIMENTS

Figure 1:
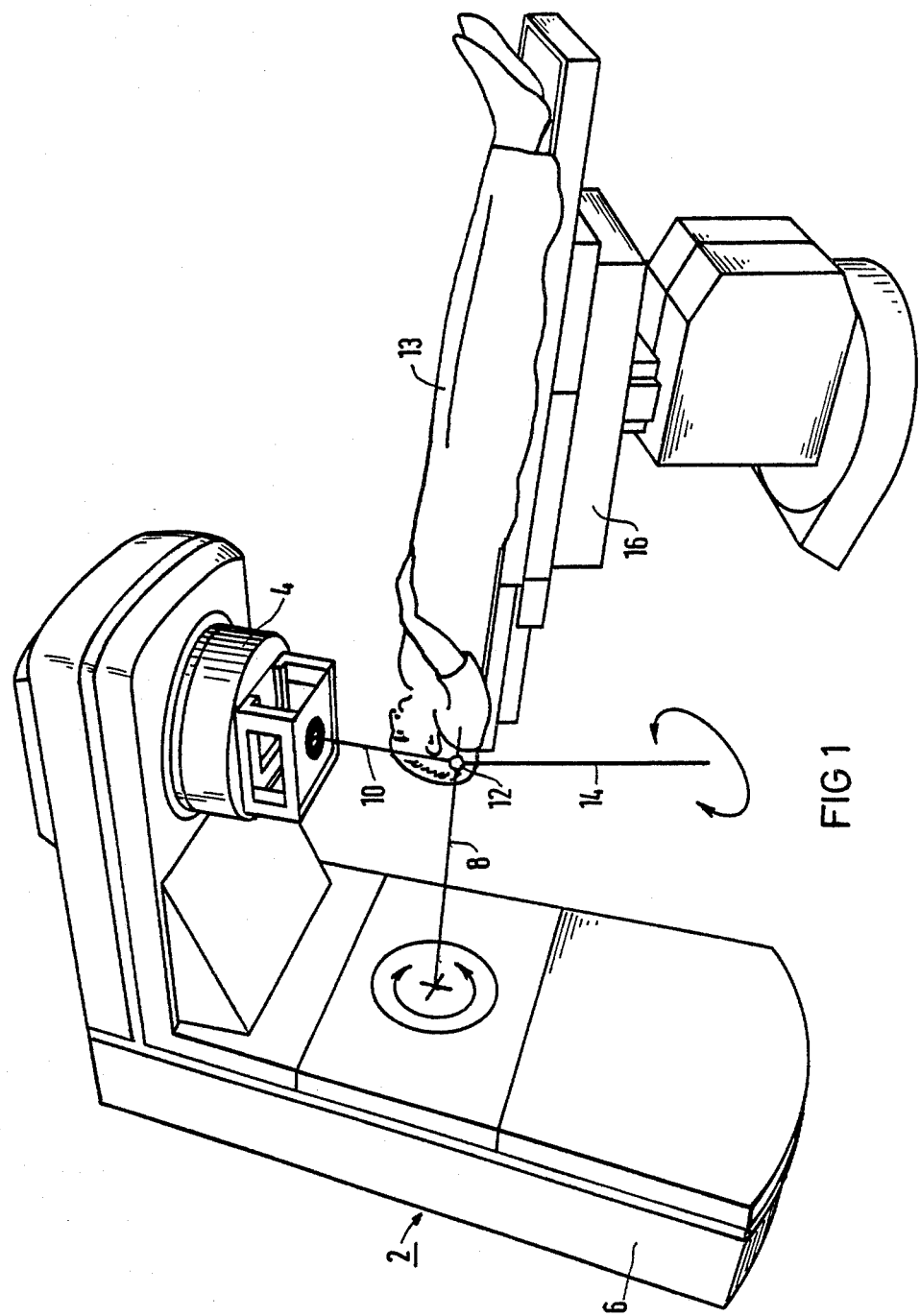
FIG. 1 is a linear accelerator wherein a contour collimator of the invention is utilized.

FIG. 1 shows a part of a known embodiment of a linear accelerator 2 wherein a contour collimator 4 having serial drive of the individual diaphragm elements in accordance with the principles of the present invention is utilized. The linear accelerator 2 has a gantry 6 which is rotated around a horizontal rotational axis 8 in the course of a theraputic treatment. The principle ray of the radiation beam emerging from the linear accelerator 2 is referenced 10. During the treatment, the ray 10 is directed onto the zone 12 of a patient 13 to be treated which lies in the isocenter. The rotational axis 8 of the gantry 6, the rotational axis 14 of a treatment table 16 and the radiation axis 10 intersect in the isocenter.

Figure 2:
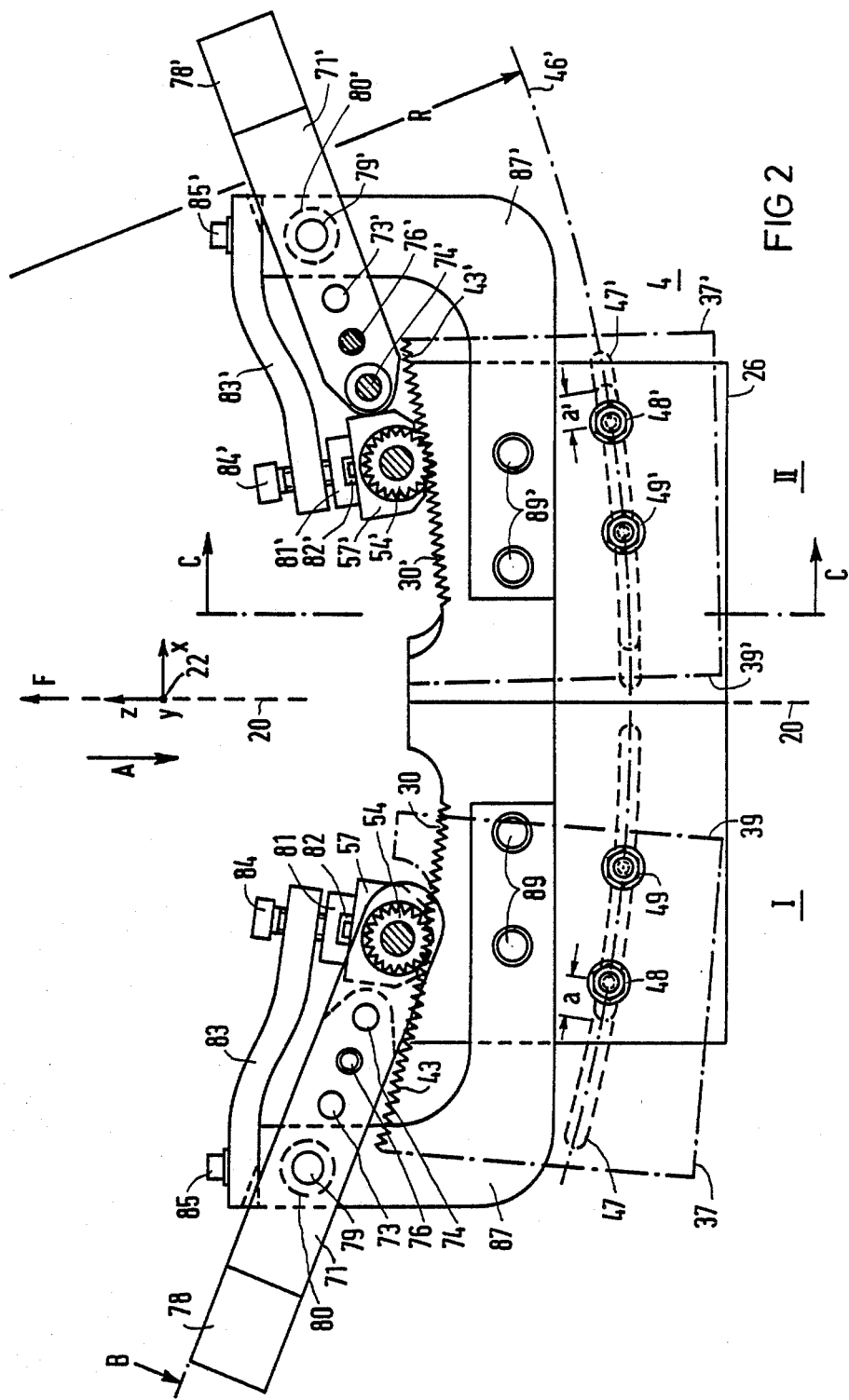
FIG. 2 is a side view of the contour collimator of the invention.

FIG. 2 shows a lateral view of details of the contour collimator 4. This is composed of two parts or sides I, II which are fashioned symmetrically relative to one another with respect to a vertical plane which proceeds through the one symmetry line 20. Given optimum adjustment, the symmetry line 20 coincides with the direction of maximum radiation of the radiation beam of high-energy radiation emanating from a focus F. In particular, this radiation can be x-radiation. As proceeds from FIG. 5 (viewed in direction A in FIG. 2), a center line 22 lies between the sides I and II, this center line 22 defining the vertical symmetry plane together with the symmetry line 20. The center line 22 coincides with the y-axis of an xyz-coordinate system. The z-axis thereof is formed by the symmetry line 20. The beam contour (profile) lying in the region of the symmetry line 20 and achieved by beam blocking out is referenced 24.

Figure 5:
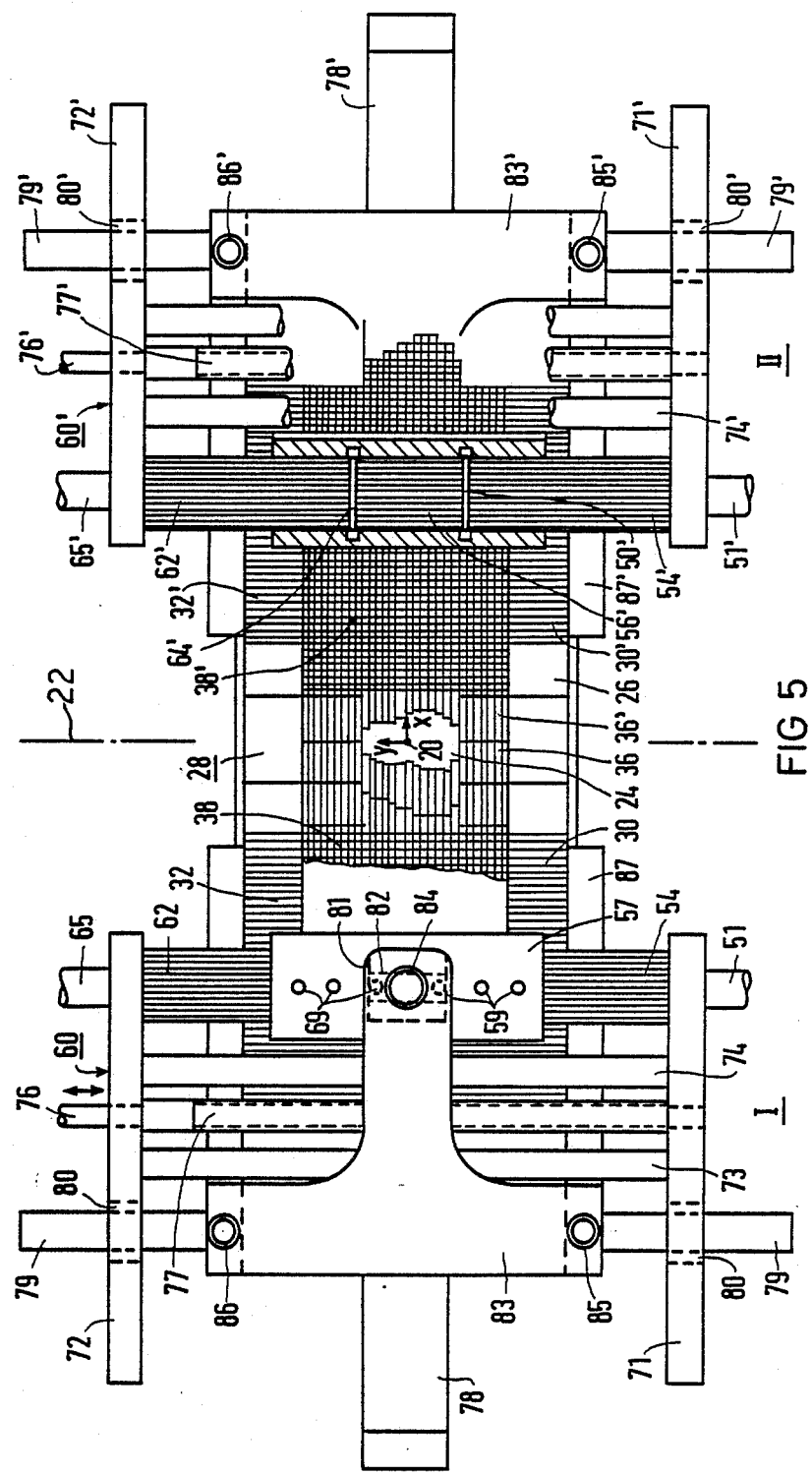
FIG. 5 is a view as seen from direction A in FIG. 2 of the contour collimator of FIG. 2, partially broken away.

As shown in FIGS. 2 and 5, first and second vertically placed, lateral outside plates 26 and 28 are arranged parallel to one another at some distance from one another. Beginning at a certain distance from the symmetry plane defined by lines 20 and 22, the upper edges of these outside plates 26 and 28 are provided with teeth 30 and 30' and 32, 32' in recesses shaped as circular arcs.

The sides I and II are symmetrically constructed with respect to the symmetry plane so that it suffices to describe only the left side I in detail. The corresponding component parts placed at the right side II are respectively provided with a prime at the allocated reference numeral. They have the same structure and the same function. They shall also be occasionally discussed below.

A packet of two groups of diaphragm plates 36 and 38 displaceable relative to one another is arranged between the two lateral outside plates 26 and 28. All diaphragm plates 36 and 38 in the front or back group are constructed in the same fashion and are arranged side-by-side. They are nonetheless provided with different reference characters because—as shall be set forth in greater detail below—they are actuated by different devices. For example, the overall packet can comprise 28 diaphragm plates 36 and 38. The same is true of the diaphragm plates 36' and 38' of the diaphragm plate packet arranged at the right.

Figures 3, 4:
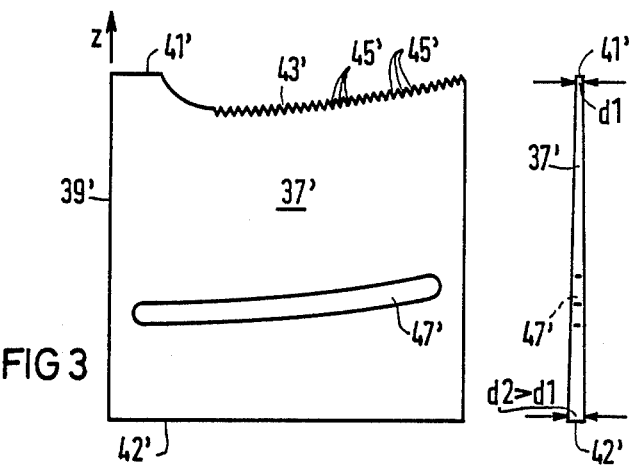
FIG. 3 is a side view of a diaphragm plate which is inserted in the right diaphragm plate packet of FIG. 2.
FIG. 4 is an end view of the straight edge of the diaphragm plate of FIG. 3 which defines the radiation beam.

One arbitrary diaphragm plate of the identical diaphragm plates 36' and 38' of the right side II is shown in greater detail in FIGS. 3 and 4 and is referenced 37'. It is essentially quadratically shaped. The straight end 39' at the left serves for limiting the radiation beam or cone. The upper edge 41' is provided with a circular arc-shaped recess in which a tooth arrangement 43' is disposed at the right. This tooth arrangement 43' preferably comprises triangular teeth 45' which are arranged at respective spacings of about 1.5 mm. As a result of this fine tooth arrangement 43', the diaphragm plates 36' and 38' can be individually pivoted and can be pivoted in fine steps parallel to the x-z plane, namely in respective steps of 1.5 mm. The tooth arrangement 43' coincides with the toothings 30' and 32' of the retained outside plates 26 and 28.

An arcuate guide channel 47' is cut into the diaphragm plate 37' below the center thereof. This curved guide channel 47' serves for the guidance of the diaphragm plate 37' such that the straight edge 39' always proceeds parallel to the outer ray of the limited radiation cone. In other words, the straight edge 37' is always directed onto the focus F of the radiation source while being guided along the guide channel 47'. The radius R of curvature for this guide channel 47' can, for example, amount to 53 cm. The radius R of curvature is entered at the swiveling arc 46' in FIG. 2.

In particular, the diaphragm plate 37' can be composed of tungsten or of a material containing tungsten such as a tungsten-nickel alloy. In accord with FIG. 4, it has a wedge-shaped cross section. In other words, the edge 41' facing the radiation source, and thus the focus F, has a thickness d1 that is smaller than the thickness d2 at that edge 42' facing away from the radiation source.

The diaphragm plates 36 and 38 of the left side I are fashioned identical to the diaphragm plates 36' and 38'. They are merely arranged side-inverted between the outside plates 26 and 28. In general, they are respectively referenced as diaphragm plate 37.

In FIG. 2, diaphragm plates 37 and 37' from the respective packets at the left and right sides I and II are shown in broken lines. Both diaphragm plates 37 and 37' are shown in a position pushed out from the middle line 22. They are shifted relative to the outside plates 26 and 28. It may also be seen in FIG. 2 that the two diaphragm plates 37, 37' are pivoted around the focus F in this position. Guide pins 48 and 49 (or 48' and 49') which connect the lateral outside plates 26 and 28 to one another serve for guidance along the guide channels 47 and 47' during swiveling (drive via the teeth arrangements 43 and 43'). When the contour collimator 4 is in a symmetrical position and entirely closed, then the straight edges 39 and 39' which are directed toward the focus F are in the symmetry plane defined by lines 20 and 22. In order, however, for the diaphragm plate 37 to be also able to travel into the region of the right side II (and, correspondingly, the diaphragm plate 37' into the region of the left side I), the guide channels 47 and 47' are executed somewhat longer than actually required for the symmetrical closed position. This is indicated by the spacing a and a' in FIG. 2. It has been shown that given a spacing $a=a'=10$ mm a diaphragm plate 37 and 37' having a base width of 10 cm can be moved adequately far into the neighboring side II or I.

A common adjustment element is provided for the prescribed plurality of diaphragm plates 30 of the front group. This serves for the serial displacement of a respectively first diaphragm plate selected from these diaphragm plates 36 relative to the remaining diaphragm plates 36. As set forth further below, this adjustment element is in engagement with the teeth of the selected diaphragm plate 36. Further, an interlock mechanism engaged with the teeth of the remaining diaphragm plates 36 of the front group is provided. There is also a mechanism for displacing the adjustment element from the teeth of the selected diaphragm plate to the tetth of a neighboring, second diaphragm plate. When the adjustment element is displaced from the first to the second diaphragm 36, the first diaphragm plate 36 is interlocked and the neighboring, second diaphragm plate 36 is unlocked. The second diaphragm plate 36 can then also be shifted relative to all diaphragm pluralized 36 that are now interlocked. Instead of this, one can also proceed to a third, fourth, etc. diaphragm plate 36 and these can be pivoted.

A corresponding adjustment element and corresponding mechanisms are also provided for the back group of diaphragm plates 38. The two mechanisms for displacing the adjustment elements are largely identical, i.e are formed by the same component parts.

The adjustment element and the interlock mechanism for the front group of diaphragm plates 36 shall be considered first; the back group shall then be considered.

Figure 6:
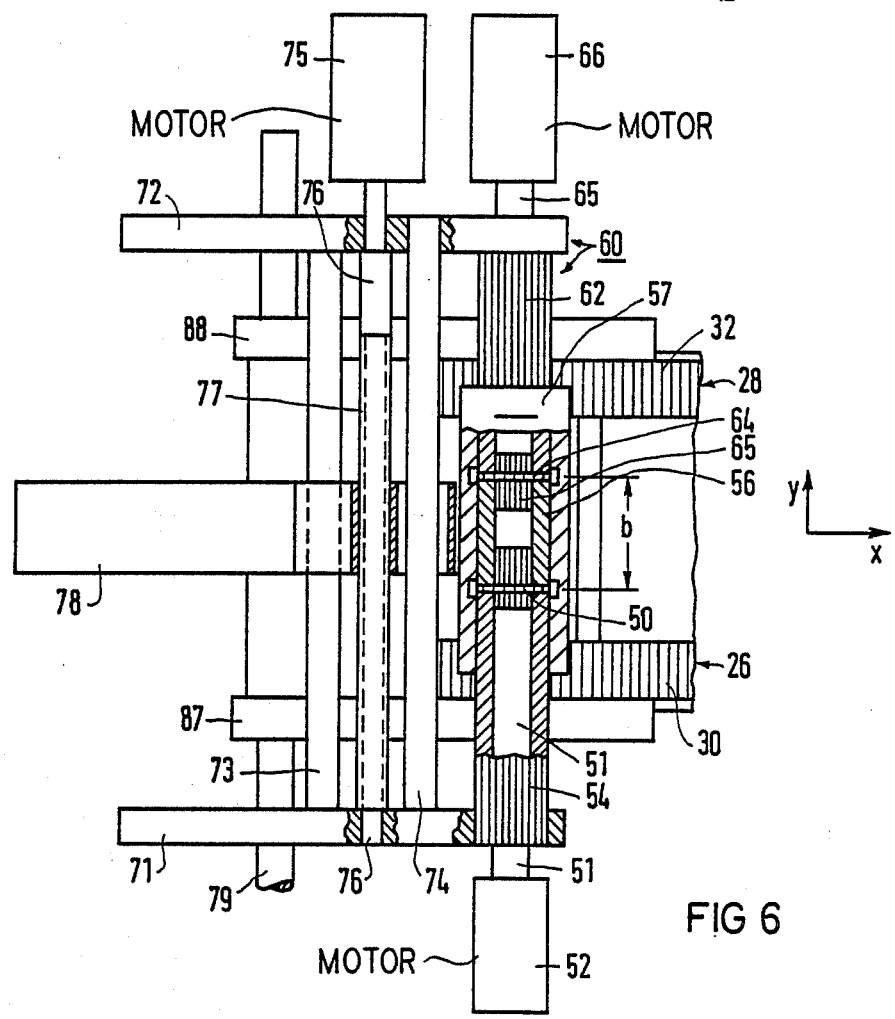
FIG. 6 is a view as seen from direction B in FIG. 2 of the left part of the contour collimator of FIG. 2 without diaphragm plates.

According to FIGS. 5 and 6, this adjustment element comprises a driving gear wheel 50 of roughly the thickness d1 of the allocated diaphragm plates 36 measured at the teeth arrangement 43 and which is in engagement with the selected diaphragm plate. This gear wheel 50 is connected to an electric motor 52, preferably to a stepping motor via an adjustment shaft 51. The adjustment shaft 51 extends roughly up to the center of the system, cf. FIG. 6. As proceeds from FIG. 7, a coupling 53 can also be arranged between the front end of the adjustment shaft 51 and the motor 52. The back end region of the adjustment shaft 51 is toothed and the drive gear wheel 50 is slipped onto this end region. When the motor 52 turns, the drive gear wheel 50 also rotates in the desired direction, whereby the selected diaphragm plate 36 is entrained via its teeth until it has assumed the desired final position.

An interlock mechanism is also provided for the adjustment element for the selected diaphragm plate 36. This interlock mechanism encompasses first and second toothed shafts 54 and 56. These two shafts 54 and 56 are broad gear wheels comprising longitudinal bores which are axially aligned with one another. The teeth coincide with the teeth 30 and 32 of the lateral plates 26 and 28 and the teeth 37 of the diaphragm plates 36 and 38. The drive gear wheel 50 lies axially between the two shafts 54 and 56. Its outside diameter as well as its teeth are respectively identical to the outside diameter and the teeth of the shafts 54 and 56. The adjustment shaft 51 is thereby conducted through the longitudinal bore of the shaft 54 and is introduced into the longitudinal bore of the shaft 56. The two shafts 54 and 56 are connected to one another by a sleeve-shaped connecting part 57 comprising a lower recess 58 (cf. FIG. 7) for enabling an engagement into the tetth arrangement 43. The fastening screws employed for this purpose and arranged at the top are referenced 59 in FIG. 5.

The two rollers or shafts 54 and 56 are part of a frame 60 and are thus not rotatable around their longitudinal axes. Of the entire section between the front end of the shaft 54 and the back end of the shaft 56, only that part which is occupied by the drive gear wheel 50 is rotatable around the longitudinal axis. The two shafts 54 and 56 thus serve for arresting the diaphragm plates 36 lying therebelow, whereas the drive gear wheel 50 is provided for swiveling, i.e for displacing the selected diaphragm plate 36 in the x-direction.

It may be seen from FIGS. 5 and 6 that a third toothed shaft 62 having the same diameter and same teeth spacing is also provided. This is axially aligned relative to the two other shafts 54 and 56. Together with the shaft 56, it serves as an interlock element for the non-selected diaphragm plates 38 of the back group. Accordingly, a second drive gear wheel 64 of the same diameter is arranged between the two shafts 56 and 62. This is seated on one end region having teeth of a second adjustment shaft 65. The second adjustment shaft 65 has its other end likewise connected to a motor 66. A coupling (not shown) can also be provided here again between the second adjustment shaft 65 and the motor 66. The motor 66 is provided for swiveling, i.e. for advancing the respectively selected, back diaphragm plate 38 parallel to the x-direction. The motor-driven swiveling ensues until the apertaining diaphragm plate 38 has assumed the desired final position.

By employing two adjustment elements 52, 51, 50 as well as 66, 65, 64 the adjustment time in which the diaphragm plates 36, 38 are set in the displacement direciion x is cut in half.

Given small fields to be irradiated, the spacing a between the two drive gear wheels 50 and 64 should be selected relatively small. Both drive units can then be utilized and the afore-mentioned, halved adjustment time then derives.

The sleeve-shaped connecting piece 57 also holds the third shaft 62 axially aligned relative to the two other shafts 54 and 56. Screws 69 are also provided at the top for fastening. These are arranged in a line parallel to the y-axis together with the screws 59. As may be seen from FIG. 6, all three shafts 54, 56 and 62 are a component part of the aforementioned frame 60.

This frame 60 is a component part of the aforementioned means for displacing the said adjustment element. It comprises first and second lateral arms 71 and 72 which are aligned parallel to the x-axis and which are rigidly connected to one another by two parallel guide rods 73 and 74, being connected in roughly their central region. The two guide rods 73 and 74 thereby have their end sides connected to the lateral arms 71 and 72. The frame 60 also includes the axial arrangement of the shafts 54, 56, 62. The toothed shafts 54 and 62 thereby have their end sides firmly connected to the respective lateral arms 71 and 72. This can ensue firmly fitting the end teeth into a hole in the respective lateral arms 71 and 72. This frame 60 is displacable by a further stepping motor 75, being displacable transversely relative to the diaphragm plates 36 and 38, i.e. in y-direction. The motor 75 for the cross-displacement is shown next to the motor 66 in FIG. 6. It is thereby connected to an adjustment spindle 76, i.e. to a rod comprising a thread 77. The adjustment spindle 76 is conducted through a hole in the second lateral arm 72 and is rotatably seated in the first lateral arm 71. It turns in a thread that is attached in a retaining block 78 transversely relative to the longitudinal direction. The retaining block 78 thereby has its longitudinal direction extending parallel to the xz-plane. The parallel arrangement of the adjustment spindel 76 between the guide rods 73 and 74 may be seen from FIGS. 2, 5 and 6. The retaining block 78 is rounded at its ends, and also accepts the guide rods 73 and 74, if necessary in respective linear ball bearings (cf. FIG. 6).

The retaining block 78 receives a shaft 79 parallel to the y-direction. The thrust shaft 79 is thereby secured to the retaining block 78 with a screw (not shown) at both sides, and is conducted through holes in the lateral arms 71 and 72 and can glide or slide therein (upon actuation of the spindle 76). When, under the influence of the motor 75, the adjustment spindle 76 rotates in one of the two directions, the entire, inherently rigid frame 60 composed of the component parts 54, 56, 57, 62, 71, 72, 73 and 74 is shifted parallel to the y-axis with the parts 50, 51, 52 and 64, 65, 66. The retaining block 78 thereby remains stationary. The displacement ensues in whole steps equal to the thickness d1 of the diaphragm plates, for example in respective whole multiples of $d1 = 3$ mm. The diaphragm plates 36 and 38 to be adjusted are selected in this way. During displacement, moreover, both gear wheels 50 and 64 are simultaneously displaced parallel to each other in the same direction, $+y$ or $-y$. To reduce the friction in the displacement parallel to the y-axis, linear ball bearings are built into the frame 60, the shaft 79 gliding through these linear ball bearings.

The three toothed shafts 54, 56, 62 together with drive wheels 50, 64 are pressed against the 43 respective teeth arrangements of the diaphragm plates 36 and 38 as well as against the teeth 30 and 32 of the respective outside plates 26 and 28 by a pressure means. This pressure means comprises a contact pressure member 81 which slides on the upper surface of the connecting part 57 upon displacement of the frame 60 in y-direction. The pressure member 81 has a slot 82 at its underside so that it is not snagged at the screws 59 and 69 when sliding.

The pressure means further comprises a contact pressure bow 83. This is fashioned T-shaped and swayed. An adjustment screw 84 which presses against the contact pressure member 81 is provided at the foot thereof. An adjustment screw 84 permits adjustment of the contact pressure of the shafts 54, 56 and 62 against the teeth 30, 32 and 43. The cooperating bearing is formed by the clamping surface between the cross arm of the T-shaped contact pressure bow 83 and the surface of lateral bows 87 and 88 in the region of the screw-connections 85 and 86.

The T-shaped contact pressure bow 82 is secured by the screw-connections 85 and 86 to the two spaced lateral bows 87 and 88 aligned parallel to one another. The two lateral bows 87 and 88 are each fashioned L-shaped and are secured to the respective outside plates 26 and 27 with respective screws 89 and 90. The lateral bows 87 and 88 thus also enclose the diaphragm plates 36 and 38 between the bows. To maintain space available for the y-displacement, the distance between the lateral bows 85 and 86 is somewhat smaller than the distance between the lateral arms 71 and 72.

The contact pressure piece 81 could be replaced by some other component part having less friction.

When one of the diaphragm plates 36 or 38 is to be displaced in x-direction, then one proceeds in the following way. The drive motor 75 for the transverse displacement is actuated first. The lateral displacement of the frame 60 in the y-direction ensues in whole steps of the thickness d1 of the diaphragm plates, for example by respectively 3 mm. In this way, the diaphragm plate to be displaced is selected, namely by one of the two drive gear wheels 50 or 64. When one of the diaphragm plates 36 or 38 has been selected, the adjustment in x-direction is undertaken. It must be emphasized that only the selected diaphragm plate 36 or 38, i.e. only that diaphragm plate which is now in engagement with the drive gear wheel 50 or 64, can be displaced. All other diaphragm plates 36 or 38 are interlocked by the three shafts 54, 56 and 62. The adjustment of the selected diaphragm ensues either via the first adjustment shaft 51, operated by the first motor 52, or ensues via the second adjustment shaft 65, operated by the drive motor 66. These adjustment shafts 51 and 65 are rotated in whole-number toothed steps until the selected diaphragm plate has reached the previously selected position in the beam profile 24.

It should also be noted that a means for reporting the displaced position of the individual diaphragm plates 36 and 38 can also be preferably provided. Such a means (not shown) can comprise a counter which counts the number of actuated teeth of the teeth arrangements 43 or 43' of the selected diaphragm plate 36 or 38 in every displacement. This can be a mechanical or optical counter, or may be a counter which counts the steps of the actuated stepping motor 52 or 66. The number of steps traversed which are characterized by electrical pulses is a measure for the positioning in x-direction.

As stated above, the shafts 54, 56 and 62 act as locking or breaking elements which retain all of the diaphragm plates 36 and 38 except two of them.

Instead, some other retaining or locking element can also be selected which engages into the tooth arrangement 43 of the diaphragm plates 37. The teeth arrangement 43 need not necessarily lie at a plate edge but may alternatively be disposed in the interior of the plate as shown in FIG. 9.

After adjusting all diaphragm plates 36 and 38, the drive gear wheels continue to reside over the last diaphragm plates 36 and 38 to be adjusted. These are held by the allocated stepping motor which is undervoltaged. Given outage of the drive unit, the last diaphragm plates at which the drive gear wheels are just situated could thus move out of their position. This is avoided in that, after the diaphragm plates are adjusted, the interlock mechanism 71 through 76 continues to travel by another half thickness of the diaphragm plates. All diaphragm plates 36 and 38 are thus mechanically locked.

A desired radiation profile 24 can be set relatively quickly with the contour collimator shown in FIGS. 2 through 7. Even when rotating the contour collimator 4 during a radiation therapy treatment, one need not fear that some of the diaphragm plates 36, 38, 36' or 38' will release from these prescribed positioning as a consequence of their weight and the radiation contour 24 will thus be changed. During such a revolution, the radiation contour can be re-adjusted in steps in selected orbital positions in order to thus apply an optimum radiation field.

As stated above, the material comprising the diaphragm plates must be radiation-resistant and radiation-impermeable and must also be able to be processed with standard working methods. For example, it is preferable to be able to cut channels and teeth in the diaphragm plates without an excessively high outlay, and it is also necessary to grind the diaphragm plates to a wedge shape. As stated above, a material which meets these requirements is, for example, a tungsten-nickel alloy. Such an alloy is a relatively inelastic material. When diaphragm plates made of such a material, however, are shifted from the center line, i.e., are moved out of the center of the radiation, the diaphragm plates can seize for geometrical reasons, making re-introduction of the plates to their original position difficult. This problem is of significance when a plurality of diaphragm plates which taper in the direction toward the point of origin of the radiation are used. A diaphragm plate structure which avoids this problem is shown in FIGS. 8 through 12.

As shown in the enlarged view of a portion of the collimator in FIG. 8, proceeding from the center line 22, the two outside plates 26 and 28 taper toward the outside, i.e. in ±x-direction. For clarity, this taper is shown exaggerated in FIG. 8. In reality, the taper is relatively slight but is of significance for the desired function. The taper beginning at both sides of the center line 22 amounts, for example, to only 0.54 mm (measured in y-direction) when progressing by about 10 cm toward the outside (in +x or −x direction), resulting in an angle equal to $5.4 \times 10^{-3}$ degrees.

The distance betwenn the two inside surfaces of the outside plates 26 and 28 increasing in the x-direction guarantees that a seizing or pinching cannot occur when driving or opening the diaphragm plates 36, 38, 36', 38' as set forth below.

The side view of one of the diaphragm plates 36' is shown in FIG. 9. This is quadratically fashioned, having an area, for example, of 10 cm × 10 cm, and has a curved guide channel 47' which serves the purpose of swiveling around the focus of the radiation source. A recess 142' accomodated in the upper part of the diaphragm plate 36' is provided with a teeth 43' at its lower edge, the teeth 43' being in engagement with the adjustment element (not shown) for sensitive swivel or displacement of the diaphragm plate 36'.

The inside surfaces of the outside plates 26 and 28 recede from one another toward the outside (in the x-direction). Seizing or pinching of the diaphragm plates 36, 38, 36' and 38' during retraction can thus be prevented. When, however, plane parallel diaphragm plates are then employed, a wobbling of the diaphragm plates could occur when moving them back or toward one another with respect to the center line 22. Clearances through which the radiation could pass would thus be created between the diaphragm plates. This must be prevented under all circumstances. In order to avoid such clearance, all diaphragm plates 36, 38, 36' and 38' are ground slightly wedge-shaped in the direction toward the center line 22. This shall be discussed below with reference to FIGS. 9 through 12.

As seen in FIGS. 9 through 12 the diaphragm plate 36' has an upper thickness d1U and a lower thickness d2U (cf. the section X—X through the left part of the diaphragm plate 36') at the edge 39' facing the center line 22 of the radiation 10, an has an upper thickness d1V and a lower thickness d2V (cf. the section XI—XI through the right part of the diaphragm plate 36') at its edge 40' facing away from the center line 22 of the radiation 10. The thickness d1V is greater than d1U; d2V is likewise greater than d2U. This is also shown in FIG. 12, i.e. at that edge 41' of the diaphragm plate 36' facing the radiation.

The wedge angle which derives when proceeding from the edge 39' to the edge 40' lies in the region of 1/100 mm or somewhat more, particularly 4/100 mm given a diaphragm plate 36' having a width of 10 cm. An adequate dimensional precision can be guaranteed when processing a material such as the aforementioned tungsten-nickel alloy.

An additional measure is that the diaphragm plates 36, 38, 36', 38' have thicknesses d1U and d1V at that edge 41' facing the radiation 10 which are smaller than the respective thicknesses d2U and d2V at that edge 42' facing away from the radiation 10. These two facts can also be expressed in the following way: The diaphragm plate 36' is ground wedge-shaped in two directions residing perpendicularly relative to one another which are established by the edges 41', 42' and 39', 40'.

In order to keep the geometrical error as low as possible, the diaphragm plates 36, 38, 36', 38' (related to the radius of the guide channel 47) are ground tapered toward the center of the radius in the present case.

Stated another way, since the diaphragm plates 36, 38, 36' and 38' have their side (for example 40' in FIG. 2) facing away from the center line 22 describing a radius in x-direction relative to the focus during the displacement in the guide channel 47, the lower corner E1 (cf. FIG. 9) of the selected upwardly tapering diaphragm plates 36' rises relative to the remaining diaphragm plates 36' and relative to the stationary outside plates 26 and 28 as the selected plates 36' are moved. When adequate play is not present, this being undesireable due to the danger of radiation throughput, seizing can occur in the diaphragm plates. In order to prevent this, the outside plates 26 and 28 are outwardly ground free (small angle $\phi$, cf. FIG. 8) by the thickness difference of the individual, upwardly rising diaphragm plates 36, 38, 36' and 38' multiplied by the plurality of diaphragm plates 36, 38, 36' and 38'.

In summary, the following can be stated regarding the exemplary embodiment shown in the drawings. Only three stepping motors 52, 66 and 75 are required for driving all diaphragm plates 36 and 38 at each side I and II or the contour collimator 4, so that the control of the overall collimator system requires only six stepping motors 52, 66, 75 and 52', 66', 75' regardless of the number of diaphragm plates.

One difference over other technical solutions to single-leaf control is that the individual diaphragm plates 36, 38 and 36', 38' of a side I or II are not driven simultaneously but successively (serially). The drive ensues in accord with the toothed rack principle whereby one drive gear wheel 50 or 64 is displaced forward in steps in the direction of the drive shafts 51 and 65 from diaphragm plate to diaphragm plate 36 and 38 for adjustment. This could be referred to as "mechanical multiplexing". During the control of a diaphragm plate, the remaining diaphragm plates are fixed in their positions by the interlock teeth (toothed racks 54 and 64). The advantage of the serial drive principle over multi-leaf collimators having parallel drive lies in the significantly simpler structure which requires less space and which, due to the low weight, can also be utilized in existing radiation therapy installations as supplementary equipment. Asymmetrical radiation fields can also be set relatively quickly and in fine steps.

The application region of irregular radiation fields practically relates only to radiation therapy techniques having fixed irradiation directions. The time requirement of a few seconds for motor-driven profile adjustment thereby plays no part. It has been shown that the dose distributions achieved with continuous moving rays can also be achieved by irradiations from many fixed irradiation directions. This is possible without further difficulty with the present multi-leaf collimator using serial drive, so that this multi-leaf collimator can be utilized in the full spectrum of radiation therapy irradiation techniques.

Although modifications and changes may be suggested by those skilled in the art it is the intention of the inventor to embody within the patent warranted hereon all changes and modificatinns as reasonably and properly come within the scope of their contribution to the art.

We claim as our invention:

1. A contour collimator for use in shaping a radiation beam comprising:
 a plurality of radiation-impermeable diaphragm plates, each plate having an engagement means;
 means for mounting said diaphragm plates side-by-side in the path of said radiation beam with each diaphragm plate being individually displaceable so as to permit passage of radiation through said collimator;
 means for selecting at least one of said diaphragm plates and for displacing said at least one diaphragm plate relative to the remaining diaphragm plates, said means for selecting and displacing being engageable with the engagement means of said at least one diaphragm plate;
 interlock means for maintaining said remainder of said diaphragm plates in their respectively existing positions during displacement of said at least one diaphragm plate, said interlock means being engageable with the engagement means of each of said remaining diaphragm plates; and
 means for changing the position of said means for selecting and displacing such that said means for selecting and displacing engages the engagement means of at least one different diaphragm plate from the at least one diaphragm plate previously displaced, said means for selecting and displacing then displacing said at least one different diaphragm plate while said interlock means maintains the remainder of said diaphragm plates in their respectively existing positions.

2. A contour collimator as claimed in claim 1, further comprising:
a further plurality of radiation-impermeable diaphragm plates, each plate in said further plurality having an engagement means;
means for mounting said further plurality of diaphragm plates with the diaphragm plates of said further plurality side-by-side in the path of said radiation beam, each diaphragm plate in said further plurality of diaphragm plates being individually displaceable so as to permit passage of radiation through said collimator, and operating in combination with said plurality of diaphragm plates to shape said radiation beam;
further means for selecting at least one of said diaphragm plates in said further plurality of diaphragm plates and for displacing said at least one diaphragm plate in said further plurality of diaphragm plates relative to the remaining diaphragm plates in said further plurality, said further means for selecting and displacing being engageable with the engagement means of said at least one diaphragm plate of said further plurality;
further interlock means for maintaining said remainder of diaphragm plates in said further plurality in their respectively existing positions during displacement of said at least one diaphragm plate in said further plurality, said further interlock means being engageable with the engagement means of each of said remaining diaphragm plates in said further plurality; and
further means for changing the position of said further means for selecting and displacing such that said further means for selecting and displacing engages the engagement means of at least one different diaphragm plate in said further plurality from the at least one diaphragm plate in said further plurality previously displaced, said further means for selecting and displacing then displacing said at least one different diaphragm plate in said further plurality while said further interlock means maintains the remainder of said diaphragm plates in said further plurality in their respectively existing positions.

3. A contour collimator as claimed in claim 2, wherein said means for changing the position of said means for selecting and displacing is engageable with the engagement means of said diaphragm plates in said further plurality of diaphragm plates, and functions as said further means for changing the position of said further means for selecting and displacing.

4. A contour collimator as claimed in claim 1, wherein said collimator has a center line, and wherein said plurality of diaphragm plates comprises two groups of diaphragm plates respectively symmetrically disposed on opposite sides of said center line, and wherein said two groups of diaphragm plates are held in said means for mounting with the respective diaphragm plates in said groups being individually displaceable toward and away from said center line.

5. A contour collimator as claimed in claim 1, wherein said engagement means is disposed at an edge of each of said diaphragm plates.

6. A contour collimator as claimed in claims 1, wherein said means for mounting further comprises means for permitting limited rotation of said diaphragm plates around a common focus.

7. A contour collimator as claimed in claim 1, wherein each of said diaphragm plates has a guide channel therein, and wherein said means for mounting includes an element engaging said guide channel.

8. A contour collimator as claimed in claim 7, wherein said guide channel is curved.

9. A contour collimator as claimed in claim 7, wherein said means engaging said guide channel comprises two guide bolts in said guide means parallel to each other and extending through said guide channels.

10. A contour collimator as claimed in claim 1, wherein said engagement means of said diaphragm plates is a plurality of teeth in each of said plates, and wherein said means for selecting and displacing includes a drive gear wheel which engages said teeth and which has a thickness substantially equal to the thickness of a diaphragm plate.

11. A contour collimator as claimed in claim 10, wherein said means for selecting and displacing further comprises a shaft connected to said drive gear wheel and to a motor for driving said drive gear wheel.

12. A contour collimator as claimed in claim 11, wherein said shaft has a free end, and wherein said drive gear wheel is secured to said shaft at said free end.

13. A contour collimator as claimed in claim 1, wherein said engagement means of said diaphragm plates is a plurality of teeth on each of said plates, and wherein said interlock means includes at least one toothed shaft engaging the teeth of at least some of said diaphragm plates.

14. A contour collimator as claimed in claim 1, wherein said means for selecting and displacing includes a driven element engageable with said engagement means of said diaphragm plates and a shaft connected to said driven element and to a motor for driving said driven element, wherein said interlock means includes a shaft also engageable with said engagement means of said diaphragm plates, and wherein said shaft of said interlock means has a longitudinal core therein in which said shaft connected to said driven element in said means for selecting and displacing is at least partially received.

15. A contour collimator as claimed in claim 2, further comprising:
a driven element in said means for selecting and displacing, said driven element engageable with said engagement means of said diaphragm plates in said plurality of diaphragm plates, and a first shaft connected to said first driven element and to a motor for driving said first driven element;
a second driven element in said further means for selecting and displacing, said second driven element being engageable with the engagement means of said diaphragm plates in said further plurality of diaphragm plates, and a second shaft connected to said second driven element and to a motor for driving said second driven element;
a first interlock shaft in said interlock means, a second interlock shaft in said further interlock means, and a central interlock shaft shared by said interlock means and said further interlock means, each of said first interlock shaft in said interlock means and said second interlock shaft in said further interlock means and said central interlock shaft having means for engaging said engagement means of said diaphragm plates in one of said plurality of diaphragm plates or said further plurality of diaphragm plates and each said first interlock shaft, said second interlock shaft, and said central interlock shaft, being axially aligned and each of said first interlock, second interlock, and central interlock shafts having a bore, said bores being axially aligned, said first interlock shaft in said interlock means receiving said first shaft in said bore of said first interlock shaft and said second interlock shaft in said further interlock means receiving said second shaft in said bore of said second interlock shaft and said central interlock shaft at least partially receiving both said first and second shafts of said second interlock shaft; and said first and second driven elements and said first and second interlock shafts in said interlock means and said further interlock means and said central interlock shaft all having the same outside diameter.

16. A contour collimator as claimed in claim 15, wherein said engagement means of said diaphragm plates in each of said plurality of diaphragm plates and said further plurality of diaphragm plates is a plurality of teeth in each diaphragm plate, wherein said first and second driven elements, said first and said second interlock shafts in said interlock means and said further interlock means, and said central interlock shaft all have teeth thereon engageable with said plurality of teeth in said diaphragm plates in each of said plurality of diaphragm plates and said further plurality of diaphragm plates and wherein said first and second driven elements and said first, said second, and said central interlock shafts all have the same number of teeth and the same tooth division.

17. A contour collimator as claimed in claim 1, wherein said means for mounting includes two outside wall plates between which said diaphragm plates are arranged substantially parallel to each other with said engagement means disposed at one edge of each of said diaphragm plates.

18. A contour collimator as claimed in claim 17, further comprising means for coupling said means for selecting and displacing to said interlock means.

19. A contour collimator as claimed in claim 1, wherein said means for selecting and displacing includes a frame and means for connection to a motor for displacement of said frame in a direction transverse to the direction of displacement of said diaphragm plates.

20. A contour collimator as claimed in claim 19, wherein said frame includes two spaced lateral arms, and wherein said interlock means includes an interlock shaft engageable with said engagement means of said diaphragm plates, said interlock shaft being disposed between and received in said lateral arms.

21. A contour collimator as claimed in claim 19, wherein said means for displacing said frame includes a threaded spindle connected to a motor and said frame further includes a retaining block connected to said frame having a threaded bore therein receiving said spindle such that said frame is transversely displaced as said spindle is rotated.

22. A contour collimator as claimed in claim 20, further comprising means for applying pressure to said interlock shaft for urging said interlock shaft into engagement with said engagement means of said diaphragm plates.

23. A contour collimator as claimed in claim 22, wherein said means for selecting and displacing includes at least one driven element engageable with said engagement means of said diaphragm plates, wherein said interlock shaft includes at least two axially aligned portions with said driven element therebetween, said portions of said interlock shaft being connected by a connecting element, and wherein said means for applying pressure is a contact pressure piece in sliding engagement with an exterior of said connecting element so as to maintain pressure thereon as said frame is transversely displaced.

24. A contour collimator as claimed in claim 22, wherein said means for mounting includes two spaced wall plates between which said diaphragm plates are disposed and wherein said means for applying pressure is a contact pressure spring attached to each of said wall plates.

25. A contour collimator as claimed in claim 19, further comprising a frame shaft on which said frame is slidably disposed for said transverse displacement thereof.

26. A contour collimator as claimed in claim 1, wherein each of said diaphragm plates has an edge facing said radiation beam and an opposite edge, and wherein said edge facing said radiation beam has a smaller thickness than said opposite edge.

27. A contour collimator as claimed in claim 1, wherein said engagement means of said diaphragm plates is a plurality of teeth, and wherein said teeth are triangularly shaped.

28. A contour collimator as claimed in claim 27, wherein said teeth on each diaphragm plate are disposed at a spacing of about 1.5 mm.

29. A contour collimator as claimed in claim 1, wherein said diaphragm plates consist of a material containing tungsten.

30. A contour collimator as claimed in claim 4, wherein each of said diaphragm plates in said two groups of diaphragm plates are individually displaceable beyond said center line.

31. A contour collimator as claimed in claim 1, further comprising means for identifying the displaced position of each of said diaphragm plates.

32. A contour collimator as claimed in claim 31, wherein said engagement means of said diaphragm plates is a plurality of teeth on each diaphragm plate, and wherein said means for identifying the displaced position of a diaphragm plate comprises means for counting the number of teeth which pass a point when said diaphragm plate moves to said displaced position.

33. A contour collimator as claimed in claim 1, wherein said diaphragm plates consist of a tungsten-nickel alloy.

34. A contour collimator as claimed in claim 1, wherein said radiation beam has a center line, and wherein said means for mounting includes a pair of wall plates with said diaphragm plates disposed therebetween, said wall plates having respective symmetrical interior surfaces tapering toward said center line to a shortest dimension between said interior surfaces, and wherein each of said diaphragm plates has an edge facing said center line and an opposite edge, said edge facing said center line of each diaphragm plate having a smaller thickness than said opposite edge of the same plate.

35. A contour collimator as claimed in claim 34, wherein each of said diaphragm plates has an edge facing said radiation beam and a further opposite edge, and wherein said edge of each plate facing said radiation beam has a smaller thickness than the further opposite edge of the same plate.

36. A contour collimator as claimed in claim 1, wherein each of said diaphragm plates has a wedge-shaped cross section in two perpendicular directions.

37. A contour collimator as claimed in claim 36, wherein said means for mounting includes two spaced wall plates between which said diaphragm plates are disposed, and wherein said radiation beam has a center line with said wall plates having respective interior surfaces with a greatest distance therebetween at a location farthest from said center line.

38. A contour collimator as claimed in claim 37, wherein each of said diaphragm plates has an upper edge closest to said radiation beam, wherein said radiation beam emanates from a radiation source having a focus disposed at a distance of about 46 cm from said upper edges of said diaphragm plates, and wherein said wall plates taper outwardly from said center line to said greatest distance at about 0.54 mm for each 10 cm of wall plate length.

39. A contour collimator for use in shaping a radiation beam, said collimator having a plane of symmetry and comprising on each side of said plane of symmetry:
- a plurality of radiation-impermeable diaphragm plates, each plate having a plurality of teeth thereon;
- means for mounting said diaphragm plates side-by-side in the path of said radiation beam with each diaphragm plate being individually displaceable so as to permit passage of radiation through said collimator;
- at least one drive gear wheel having teeth engageable with said teeth of said diaphragm plates and carried on a shaft connected to a motor which rotates said shaft and said drive gear wheel to displace one of said diaphragm plates;
- at least one interlock shaft having exterior teeth for engaging said teeth of said diaphragm plates, said interlock shaft having a bore therein in which said shaft carrying said drive gear wheel is rotatably received, said interlock shaft retaining a remainder of said diaphragm plates in their respectively existing positions during displacement of said one diaphragm plate;
- a frame on which said interlock shaft and said shaft carrying said drive gear wheel are mounted; and
- means for selectively displacing said frame transversely to the direction of displacement of said diaphragm plates for positioning said drive gear wheel in engagement with a selected one of said diaphragm plates to be displaced.

40. A contour collimator as claimed in claim 39, wherein said shaft carrying said drive gear wheel extends into said bore in said interlock shaft from one side thereof, and further comprising:
- a second shaft carrying a second drive gear wheel thereon, said second drive gear wheel having teeth engageable with another of said diaphragm plates to be displaced simultaneously with the diaphragm plate engaging said drive gear wheel, said further shaft extending into an opposite side of said bore in said interlock shaft and said further shaft is connected to a motor which rotates said further shaft and said further drive gear wheel independently of said shaft and said drive gear wheel.

* * * * *